(12) United States Patent
Weinstein et al.

(10) Patent No.: US 9,572,512 B2
(45) Date of Patent: Feb. 21, 2017

(54) METHODS AND SYSTEMS FOR DETERMINING FLUID CONTENT OF TISSUE

(71) Applicant: KYMA MEDICAL TECHNOLOGIES LTD., Tel Aviv (IL)

(72) Inventors: Uriel Weinstein, Mazkeret Batya (IL); Assaf Bernstein, Givat Nilly (IL); Eyal Cohen, Ariel (IL)

(73) Assignee: KYMA MEDICAL TECHNOLOGIES LTD., Kfar Saba (IL)

( * ) Notice: Subject to any disclaimer, the term of this patent is extended or adjusted under 35 U.S.C. 154(b) by 94 days.

(21) Appl. No.: 14/621,252

(22) Filed: Feb. 12, 2015

(65) Prior Publication Data

US 2015/0150477 A1    Jun. 4, 2015

Related U.S. Application Data

(63) Continuation of application No. 12/759,715, filed on Apr. 14, 2010, now Pat. No. 8,989,837, which is a
(Continued)

(51) Int. Cl.
*A61B 5/00* (2006.01)
*A61B 5/05* (2006.01)
(Continued)

(52) U.S. Cl.
CPC ............... *A61B 5/0507* (2013.01); *A61B 5/05* (2013.01); *A61B 5/08* (2013.01); *A61B 5/1107* (2013.01);
(Continued)

(58) Field of Classification Search
CPC ............... A61B 2560/0412; A61B 2562/0209; A61B 2562/14; A61B 2562/166; A61B 5/0402; A61B 5/05; A61B 5/0507; A61B 5/08; A61B 5/1107; A61B 5/4878; A61B 5/6823; A61B 5/7285; A61B 8/085; A61B 8/4254; A61N 1/36578
See application file for complete search history.

(56) References Cited

U.S. PATENT DOCUMENTS 4,344,440 A   8/1982   Aaby et al.
4,557,272 A   12/1985  Carr
(Continued)

FOREIGN PATENT DOCUMENTS

WO    WO 2008148040 A1    12/2008
WO    WO 2009031149 A2    3/2009
(Continued)

OTHER PUBLICATIONS

Haude et al., Intracoronary Doppler—and Quantitative Coronary Angiography-Derived Predictors of Major Adverse Cardiac Events After Stent Implantation, Mar. 6, 2001, Circulation, vol. 103(9), p. 1212-1217.
(Continued)

*Primary Examiner* — Mark Remaly
(74) *Attorney, Agent, or Firm* — Cooley LLP (57) ABSTRACT

Diagnostic apparatus includes a plurality of antennas, which are configured to be disposed at different, respective locations on a thorax of a living body so as to direct radio frequency (RF) electromagnetic waves from different, respective directions toward a heart in the body and to output RF signals responsively to the waves that are scattered from the heart. Processing circuitry is configured to process the RF signals over time so as to provide a multi-dimensional measurement of a movement of the heart.

11 Claims, 8 Drawing Sheets

Related U.S. Application Data continuation-in-part of application No. PCT/IB2009/055438, filed on Dec. 1, 2009.

(51) Int. Cl.
| | |
|---|---|
| *A61B 5/11* | (2006.01) |
| *A61B 8/00* | (2006.01) |
| *A61B 5/08* | (2006.01) |
| *A61B 8/08* | (2006.01) |
| *A61B 5/0402* | (2006.01) |
| *A61N 1/365* | (2006.01) |

(52) U.S. Cl.
CPC ............ *A61B 5/4878* (2013.01); *A61B 8/085* (2013.01); *A61B 8/4254* (2013.01); *A61B 5/0402* (2013.01); *A61B 5/6823* (2013.01); *A61B 5/7285* (2013.01); *A61B 2560/0412* (2013.01); *A61B 2562/0209* (2013.01); *A61B 2562/14* (2013.01); *A61B 2562/166* (2013.01); *A61N 1/36578* (2013.01)

(56) References Cited

U.S. PATENT DOCUMENTS

| | | |
|---|---|---|
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,958,638 A | 9/1990 | Sharpe |
| 5,109,855 A | 5/1992 | Guner |
| 5,394,882 A | 3/1995 | Mawhinney |
| 5,540,727 A | 7/1996 | Tockman et al. |
| 5,549,650 A | 8/1996 | Bornzin et al. |
| 5,704,355 A | 1/1998 | Bridges |
| 5,807,257 A | 9/1998 | Bridges |
| 5,829,437 A | 11/1998 | Bridges |
| 5,967,986 A | 10/1999 | Cimochowski et al. |
| 6,019,724 A | 2/2000 | Gronningsaeter et al. |
| 6,061,589 A | 5/2000 | Bridges et al. |
| 6,064,903 A | 5/2000 | Riechers et al. |
| 6,093,141 A | 7/2000 | Mosseri et al. |
| 6,193,669 B1 | 2/2001 | Degany et al. |
| 6,233,479 B1 | 5/2001 | Haddad et al. |
| 6,330,479 B1 | 12/2001 | Stauffer |
| 6,454,711 B1 | 9/2002 | Haddad et al. |
| 6,526,318 B1 | 2/2003 | Ansarinia |
| 6,592,518 B2 | 7/2003 | Denker et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frantz et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,295,920 B2 | 10/2012 | Bouton et al. |
| 8,352,015 B2 | 1/2013 | Bernstein et al. |
| 2002/0032386 A1 | 3/2002 | Sackner et al. |
| 2002/0045836 A1 | 4/2002 | Alkawwas |
| 2003/0088180 A1 | 5/2003 | Van Veen et al. |
| 2004/0015087 A1 | 1/2004 | Boric-Lubecke et al. |
| 2004/0077952 A1 | 4/2004 | Rafter et al. |
| 2004/0249257 A1 | 12/2004 | Tupin et al. |
| 2004/0261721 A1 | 12/2004 | Steger |
| 2005/0038503 A1 | 2/2005 | Greenhalgh et al. |
| 2005/0245816 A1 | 11/2005 | Candidus et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0123770 A1 | 5/2007 | Bouton et al. |
| 2007/0135721 A1 | 6/2007 | Zdeblick |
| 2007/0152812 A1 | 7/2007 | Wong et al. |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0097199 A1 | 4/2008 | Mullen |
| 2008/0129511 A1 | 6/2008 | Yuen et al. |
| 2008/0167566 A1 | 7/2008 | Unver et al. |
| 2008/0169961 A1 | 7/2008 | Steinway et al. |
| 2008/0200802 A1 | 8/2008 | Bhavaraju et al. |
| 2008/0224688 A1 | 9/2008 | Rubinsky et al. |
| 2008/0269589 A1 | 10/2008 | Thijs et al. |
| 2008/0294036 A1 | 11/2008 | Hoi et al. |
| 2009/0048500 A1 | 2/2009 | Corn |
| 2009/0076350 A1 | 3/2009 | Bly et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0281412 A1 | 11/2009 | Boyden et al. |
| 2009/0299175 A1 | 12/2009 | Bernstein et al. |
| 2010/0056907 A1 | 3/2010 | Rappaport et al. |
| 2010/0256462 A1 | 10/2010 | Rappaport et al. |
| 2011/0130800 A1 | 6/2011 | Weinstein et al. |

FOREIGN PATENT DOCUMENTS

| | | |
|---|---|---|
| WO | WO 2009031150 A2 | 3/2009 |
| WO | WO 2009152625 A1 | 12/2009 |
| WO | WO 2011067623 A1 | 6/2011 |

OTHER PUBLICATIONS

Beyer-Enke et al., Intra-arterial Doppler Flowmetry in the superficial femoral artery following angioplasty., 2000, European Radiology, vol. 10, No. 4, p. 642-649.

Ringer et al., Follow-up on Stented Carotid Arteries by Doppler Ultrasound, Sep. 2002, Neurosurgery, vol. 51, No. 3, p. 639-643.

Kantarci et al, Follow-Up of Extracranial Vertebral Artery Stents with Doppler Sonography., Sep. 2006, American Journal of Roentgenology, vol. 187, p. 779-787.

Ghosh , et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.

Miura et al., "Time Domain Reflectometry: Measurement of Free Water in Normal Lung and Pulmonary Edema," *American Journal of Physiology—Lung Physiology* 276:1 (1999), pp. L207-L212.

Larsson et al., "State Diagrams of the Heart—a New Approach to Describing Cardiac Mechanics", Cardiovascular Ultrasound 7:22 (2009).

Bell, et al., "A Low-Profile Archimedean Spiral Antenna Using an EBG Ground Plane", IEEE Antennas and Wireless Propagation Letters 3, pp. 223-226 (2004).

International Patent Application # PCT/IB2009/055438 "Locating Features in the Heart Using Radio Frequency Imaging", filed on Dec. 1, 2009.

Ascension Technology Corporation, "TrakSTAR Adds Versatility to Ascension's New Product Line: Desktop Model Joins driveBAY Tracker for Fast Guidance of Miniaturized Sensors", USA, Apr. 7, 2008.

(56) References Cited

OTHER PUBLICATIONS

International Application PCT/IB2009/055438 Search Report dated Jul. 20, 2010.
Claron Technology Inc., "MicronTracker 3 : A New Generation of Optical Trackers", Canada, 2009.
Immersion Corporation, "Immersion Introduces New 3D Digitizing Product—MicroScribe G2; Faster Data Transfer, USB Compatibility, New Industrial Design", Press Release, San Jose, USA, Jul. 1, 2002.
Polhemus, "Fastrak: The Fast and Easy Digital Tracker", USA, 2008.
Czum et al., "The Vascular Diagnostic Laboratory", The Heart & Vascular Institute Newsletter, vol. 1, USA, Winter 2001.
Lal et al., "Duplex ultrasound velocity criteria for the stented carotid artery", Journal of Vascular Surgery, vol. 47, No. 1, pp. 63-73, Jan. 2008.
International Application PCT/IB2010/054861 Search Report dated Apr. 5, 2011.
Lin, J.C. et al., "Microwave Imaging of Cerebral Edema", Proceedings of the IEEE, IEEE, NY,US, vol. 70, No. 5, May 1, 1982, pp. 523-524.
Guido Biffi Gentili et al., "A Versatile Microwave Plethysmorgraph for the Monitoring of Physiological Parameters", IEEE Transactions on Biomedical Engineering, IEEE Service Center, Piscataway, NJ, US, Vo. 49, No. 10, Oct. 1, 2002.
Pederson, P.C. et al., "Microwave Reflection and Transmission Measurements for Pulmonary Diagnosis and Monitoring", IEEE Transactions on Biomedical Engineering, IEEE Service Center , Piscataway, NJ, US, vol. BME-19, No. 1, Jan. 1, 1978, pp. 40-48.
Supplementary European Search Report for Application No. EP 10834292.4 (PCT/IB2010/054861) dated Dec. 4, 2014.

METHODS AND SYSTEMS FOR DETERMINING FLUID CONTENT OF TISSUE

CROSS-REFERENCE TO RELATED APPLICATION

This application is a continuation of U.S. patent application Ser. No. 12/759,715, filed Apr. 14, 2010, titled "METHODS AND SYSTEMS FOR DETERMINING FLUID CONTENT OF TISSUE", which in turn is a continuation-in-part of PCT patent application PCT/IB2009/055438, filed Dec. 1, 2009, whose disclosures are incorporated herein by reference in their entireties.

FIELD OF THE INVENTION

The present invention relates generally to methods and systems for medical diagnostic measurement and monitoring, and specifically to radio frequency (RF)-based measurement and monitoring of the heart.

BACKGROUND OF THE INVENTION

RF imaging is best known in the context of radar systems, but RF diagnostic imaging and measurement systems have also been developed for medical applications. For example, U.S. Patent Application Publication 2008/0169961, whose disclosure is incorporated herein by reference, describes computerized tomography using radar, which may be used for generating an image of living tissue.

As another example, U.S. Patent Application Publication 2009/0299175, whose disclosure is incorporated herein by reference, describes a method and apparatus for determining and tracking the location of a metallic object in a living body, using a radar detector adapted to operate on a living body. Applications described in this publication include determination of the extent of in-stent restenosis, performing therapeutic thrombolysis, and determining operational features of a metallic implant.

Yet another example is U.S. Pat. No. 5,766,208, whose disclosure is incorporated herein by reference. This patent describes a non-acoustic pulse-echo radar monitor, which is employed in the repetitive mode, whereby a large number of reflected pulses are averaged to produce a voltage that modulates an audio oscillator to produce a tone that corresponds to the heart motion. The monitor output potential can be separated into a cardiac output indicative of the physical movement of the heart, and a pulmonary output indicative of the physical movement of the lung.

U.S. Pat. No. 4,926,868, whose disclosure is incorporated herein by reference, describes a method and apparatus for cardiac hemodynamic monitoring based on the complex field amplitudes of microwaves propagated through and scattered by thoracic cardiovascular structures, particularly the heart chambers, as a function of time during the cardiac cycle. The apparatus uses conformal microstrip antennas that operate in the UHF band. The basic measurement technique is vector network analysis of the power wave scattering parameter.

U.S. Patent Application Publication 2009/0240133, whose disclosure is incorporated herein by reference, describes a radio apparatus and method for non-invasive, thoracic radio interrogation of a subject for the collection of hemodynamic, respiratory and/or other cardiopulmonary related data. A radio transmitter transmits an unmodulated radio interrogation signal from an antenna into a subject, and a radio receiver captures, through the antenna, reflections of the transmitted radio interrogation signal returned from the subject. A Doppler component of the reflections contains the data that can be extracted from the captured reflections.

SUMMARY OF THE INVENTION

Embodiments of the present invention that are described hereinbelow provide methods and devices for assessment of cardiovascular function by transmission and detection of RF waves through the body.

There is therefore provided, in accordance with an embodiment of the present invention, diagnostic apparatus, including a plurality of antennas, which are configured to be disposed at different, respective locations on a thorax of a living body so as to direct radio frequency (RF) electromagnetic waves from different, respective directions toward a heart in the body and to output RF signals responsively to the waves that are scattered from the heart. Processing circuitry is configured to process the RF signals over time so as to provide a multi-dimensional measurement of a movement of the heart.

In some embodiments, the plurality of antennas includes at least three antennas, and the respective locations are chosen so as to at least partially surround the thorax.

In disclosed embodiments, each antenna has a front surface, which is configured to contact an outer surface of the body and includes a planar antenna element. The planar antenna element may include a conductive spiral. Additionally or alternatively, each antenna may include a ground plane behind the front surface with an electromagnetic band gap (EBG) structure between the ground plane and the front surface. Typically, a dielectric gel is applied between the antenna and the outer surface of the body.

In one embodiment, each antenna is configured to contact an outer surface of the body and, the processing circuitry is configured to receive and process an electrocardiogram signal received from the body by at least one of the antennas, in addition to the RF signals.

In a disclosed embodiment, the apparatus includes excitation circuitry, which is coupled to select different ones of the antennas to serve as transmitting and receiving antennas and to apply a RF excitation waveform at multiple different frequencies to the selected transmitting antennas, while the processing circuitry receives the RF signals from the selected receiving antennas, wherein the transmitting and receiving antennas and the different frequencies are selected according to a predetermined temporal pattern. Typically, the excitation circuitry includes a driver circuit, which is configured to generate the RF excitation waveform with a variable frequency, and a switching matrix, which is configured to select sets of the antennas in alternation, each set including at least one transmitting antenna and at least one receiving antenna, and for each selected set, to couple the driver circuit to excite the at least one transmitting antenna at a selected frequency while coupling the processing circuitry to receive the RF signals from the at least one receiving antenna.

In one embodiment, the plurality of antennas includes at least first and second antennas disposed on respective opposite sides of the thorax, so that the second antenna receives the RF electromagnetic waves transmitted by the first antenna after passage of the RF electromagnetic waves through at least one lung in the body, and the processor is configured to process the RF signals output by the second antenna so as to assess an amount of fluid accumulation in the at least one lung.

In another embodiment, the apparatus includes at least one pacing electrode, wherein the processing circuitry is configured to drive the at least one pacing electrode so as to pace the heart responsively to the measurement of the movement of the heart.

In yet another embodiment, the processing circuitry is configured to compare the measure of the movement of the heart before, during and after heart stress.

There is also provided, in accordance with an embodiment of the present invention, diagnostic apparatus, including an antenna, which is configured to be disposed on a thorax of a living body so as to direct radio frequency (RF) electromagnetic waves toward a heart in the body while sweeping the waves over multiple different frequencies and to output an ultra-wideband RF signal responsively to the waves that are scattered from the heart. Processing circuitry is configured to process the RF signal over time so as to provide a measurement of a movement of the heart.

In some embodiments, the apparatus includes a package, which contains the antenna and the processing circuitry and is configured to be affixed as a patch to an outer surface of the body. The apparatus may include a conductive element associated with the package, which is configured to receive electrocardiogram (ECG) signals from the outer surface of the body. Additionally or alternatively, the apparatus includes a wireless communication interface for communicating with a remote console.

There is additionally provided, in accordance with an embodiment of the present invention, diagnostic apparatus, including one or more antennas, which are configured to be disposed on a thorax of a living body so as to direct radio frequency (RF) electromagnetic waves through a lung in the body and to output RF signals responsively to the waves that have passed through the lung. Processing circuitry is configured to process the RF signals over time so as to measure RF path characteristic of the RF electromagnetic waves and, based on the path characteristic, to assess a fluid content of the lung.

The processing circuitry may be configured to measure a change in the path characteristic over one or more respiratory cycles of the lung, and to assess the fluid content responsively to the change.

In disclosed embodiments, the path characteristic includes an effective RF path length of the RF electromagnetic waves through the body. In some embodiments, the processing circuitry is configured to receive a measure of a physical distance traversed by the RF electromagnetic waves through the thorax, and to compare the effective RF path length to the physical distance in order to assess the amount of the fluid accumulation. In one embodiment, the one or more antennas include a transmitting antenna at a first location on a first side of the thorax, which transmits the RF electromagnetic waves through the lung, and a receiving antenna, which receives the waves that have passed through the lung at a second location on a second side of the thorax, opposite the first side, and the physical distance is measured between the first and second locations.

Alternatively, the one or more antennas include at least one antenna that is configured to direct the RF electromagnetic waves through the lung toward a heart in the body, and to output the RF signals responsively to the RF electromagnetic waves reflected from the heart. The apparatus may include an ultrasonic transducer, which is adjacent to the at least one antenna and is configured to direct ultrasonic waves toward the heart and receive the ultrasonic waves reflected from the heart so as to provide a measure of the physical distance.

Additionally or alternatively, the path characteristic includes an amplitude of the RF signals.

There is further provided, in accordance with an embodiment of the present invention, diagnostic apparatus, including an antenna unit, which has a front surface configured to be brought into contact with an outer surface of a living body. The antenna unit includes a planar antenna element, which is configured to direct radio frequency (RF) electromagnetic waves from the front surface into the body and to output RF signals responsively to the waves that are scattered from within the body, and a conductive element, which is configured to receive electrocardiogram (ECG) signals from the outer surface of the body. A cable is connected to the antenna unit so as to communicate with the planar antenna element and the conductive element. Processing circuitry is connected to the cable so as to receive and process the RF and ECG signals.

Typically, the apparatus includes a diplexer coupled between the cable and the processing circuitry for separating the RF signals from the ECG signals.

The antenna unit may include an adhesive patch for attachment to the body. Alternatively, the antenna unit may be configured to be worn on the body as part of a garment.

In a disclosed embodiment, the antenna unit is coated with metal and electrolytes.

There is moreover provided, in accordance with an embodiment of the present invention, diagnostic apparatus, including an antenna unit, which has a front surface configured to be brought into contact with an outer surface of a living body. The antenna unit includes a planar antenna element, which is formed on the front surface and is configured to direct radio frequency (RF) electromagnetic waves into the body and to output RF signals responsively to the waves that are scattered from within the body, with a ground plane behind the front surface and an electromagnetic band gap (EBG) structure between the ground plane and the front surface. Processing circuitry is coupled to the antenna unit so as to receive and process the RF signals.

There is furthermore provided, in accordance with an embodiment of the present invention, therapeutic apparatus, including at least one pacing electrode, configured to apply a pacing signal to a heart in a living body. One or more antennas are configured to be disposed on a thorax of the body so as to direct radio frequency (RF) electromagnetic waves toward the heart and to output RF signals responsively to the waves that are scattered from the heart. Processing circuitry is configured to process the RF signals over time so as to measure a movement of the heart and to drive the at least one pacing electrode so as to pace the heart responsively to the measured movement.

There is also provided, in accordance with an embodiment of the present invention, a method for diagnosis, including directing radio frequency (RF) electromagnetic waves from a plurality of antennas, which are disposed at different, respective locations on a thorax of a living body, toward a heart in the body from different, respective directions, and outputting RF signals responsively to the waves that are scattered from the heart. The RF signals are processed over time so as to provide a multi-dimensional measurement of a movement of the heart.

There is additionally provided, in accordance with an embodiment of the present invention, a method for diagnosis, including directing radio frequency (RF) electromagnetic waves from an antenna, which is disposed on a thorax of a living body, toward a heart in the body while sweeping the waves over multiple different frequencies, and outputting an ultra-wideband RF signal responsively to the waves that are scattered from the heart. The RF signal is processed over time so as to provide a measurement of a movement of the heart.

There is further provided, in accordance with an embodiment of the present invention, a method for diagnosis, including directing radio frequency (RF) electromagnetic waves from one or more antennas disposed on a thorax of a living body so that the waves pass through a lung in the body, and outputting RF signals responsively to the waves that have passed through the lung. The RF signals are processed over time so as to measure a RF path characteristic of the RF electromagnetic waves and, based on the path characteristic, to assess a fluid content of the lung.

There is moreover provided, in accordance with an embodiment of the present invention, a method for diagnosis, including bringing a front surface of an antenna unit into contact with an outer surface of a living body. The antenna unit included a planar antenna element and a conductive element, which is configured to receive electrocardiogram (ECG) signals from the outer surface of the body. The planar antenna element is driven to direct radio frequency (RF) electromagnetic waves from the front surface into the body and to output RF signals responsively to the waves that are scattered from within the body. Both the RF and the ECG signals from the antenna unit are received and processed.

There is furthermore provided, in accordance with an embodiment of the present invention, a therapeutic method, including directing radio frequency (RF) electromagnetic waves toward a heart in a living body from one or more antennas disposed on a thorax of the body, and outputting RF signals responsively to the waves that are scattered from the heart. The RF signals are processed over time so as to measure a movement of the heart, and the heart is paced responsively to the measured movement.

The present invention will be more fully understood from the following detailed description of the embodiments thereof, taken together with the drawings in which:

DETAILED DESCRIPTION OF EMBODIMENTS

Overview

PCT Patent Application PCT/IB2009/055438, whose disclosure is incorporated herein by reference, describes the use of radar imaging techniques to identify and locate features in the body, based on the difference in their complex dielectric constant relative to the dielectric constant of the surrounding tissue. In the disclosed embodiments, an array of antennas (also referred to as antenna elements) directs RF electromagnetic waves toward the heart and receives the waves that are scattered from within the body. Excitation circuitry applies a RF excitation waveform at multiple different frequencies to different transmitting antennas in the array. Processing circuitry receives and processes signals from different receiving antenna elements in order to locate a feature or features of interest, and possibly to track the movement of such features over the course of the heart cycle. The selection of transmitting and receiving antennas, as well as the selection of excitation frequency, follows a predetermined temporal pattern, which may be implemented by a switching matrix connected to the antenna elements.

As a result of this scheme of excitation and reception, the processing circuitry receives and processes signals from multiple spatial channels (corresponding to different pairs of antennas) at multiple different frequencies for each channel. Taken together in the time domain, these multi-frequency signals are equivalent to short pulses of RF energy. To reconstruct a three-dimensional (3D) image of the interior of the body and find the location of a feature or features, the processing circuitry applies a spatial transform to the set of received signals. The transform may, for example, comprise an inverse spherical Radon transform or an algebraic approximation of such a transform.

Embodiments of the present invention that are described hereinbelow apply techniques similar to those described in PCT/IB2009/055438 for purposes of cardiovascular diagnosis and therapy. In one embodiment, multiple antennas are disposed at different, respective locations on the thorax of a patient, typically surrounding all or at least a part of the thorax. The antennas direct RF waves from different, respective directions toward the heart and output RF signals in response to the scattered waves that they receive. The RF signals received over time are processed so as to provide a multi-dimensional (two- or even three-dimensional) measurement of movement of the heart. This approach can give a picture of heart wall movement that resembles the sort of information provided by cardiac ultrasound imaging, but does not require the active involvement of an expert operator and can even be carried out over a long period while the patient is ambulatory.

Heart wall motion measured by embodiments of the present invention provides detailed diagnostic information regarding functioning of the heart muscle. For example, the heart motion information is useful in diagnosis and monitoring of cardiac ischemia and heart failures, and can also give an indication of cardiac performance, such as chamber volume or ejection fraction. The information provided by embodiments of the present invention can be used in diagnosis, as well as prediction, of ischemic disease and/or ischemic events, such as acute myocardial infarction. The heart wall motion may be compared before, during and after heart stress caused by physical exercise or by medication, in a manner similar to ECG-based stress testing.

As yet another example, the heart wall motion information provided by embodiments of the present invention may be used in place of ultrasonic imaging data in analyzing and diagnosing cardiac mechanical function. For instance, radar-based measurements may be used instead of the Doppler imaging techniques described by Larsson et al., in "State Diagrams of the Heart—a New Approach to Describing Cardiac Mechanics," *Cardiovascular Ultrasound* 7:22 (2009), which is incorporated herein by reference.

Additionally or alternatively, embodiments of the present invention can be used in long-term monitoring of heart conditions, and particularly as an ambulatory monitor for the detection of "silent ischemias" in coronary artery disease. Heart wall motion monitoring of this sort can thus be used as a diagnostic tool in addition to or instead of conventional stress testing or Holter monitoring.

The heart motion information provided by embodiments of the present invention may also be used for therapeutic purposes. For example, in one embodiment, a pacemaker is driven to pace the heart based on this sort of measurement, as an addition to other parameters, so that the amplitude and timing of the pacing signal give an optimal result in terms of the actual profile of contraction of the heart muscle. This sort of approach can be particularly useful in cardiac resynchronization therapy.

In some embodiments, these RF-based techniques are used to assess fluid accumulation in the lungs, typically for diagnosis and follow-up of pulmonary edema or lung congestion. In these embodiments, one or more antennas on the thorax direct RF waves through one (or both) of the lungs and output RF signals in response to the waves that have passed through the lung. The RF signals are processed over time in order to measure a path characteristic of the RF waves passing through the body, such as the effective RF path length of the RF waves. The RF path length, as opposed to the actual, physical distance, is defined by the length of time required for the waves to pass through the chest (either directly, from one side to the other, or by reflection from the heart and return to an antenna). This path length depends on the dielectric constant of the tissue along the path. When there is fluid in the lungs, the dielectric constant is greater (relative to normal, air-filled lungs), and the RF path length increases accordingly. This RF path length may thus be used to assess the fluid content of the lung.

In some embodiments, monitoring information is sent from a local controller attached to the antennas on the patient's body to a center where is the information can be accessed by a referring physician, experts, technicians, and/or the patient himself. The data may flow via a local gateway device, such as a cell-phone or personal computer, via a network, such as the Internet or telephone network, to the center, where it is stored.

Various types of antennas may be used in implementing embodiments of the present invention, including the sort of cavity-backed antenna that is described in PCT/IB2009/055438. Alternatively, some embodiments of the present invention use a planar antenna comprising a conductive spiral, which is formed on the front surface of the antenna. The antenna is backed by an in-phase reflective structure based on an electromagnetic band gap (EBG) structure between the antenna ground plane and the front surface. This design provides a flat, possibly flexible antenna, which can be fixed to the body surface by a gel or other adhesive. (Suitable types of gels for this purpose are described in PCT/IB2009/055438.) The antenna may also comprise a conductive element, which receives electrocardiogram (ECG) signals from the body surface along with the RF signals output by the antenna itself. The antenna thus performs two complementary measurements simultaneously and obviates the need for separate ECG electrodes.

In one embodiment, the antenna is part of a self-contained patch that also includes radar processing circuits and a power source. The patch may also include a transmitter, such as a wireless unit, for transmission of data to a monitor or gateway.

System Description

Figure 1:
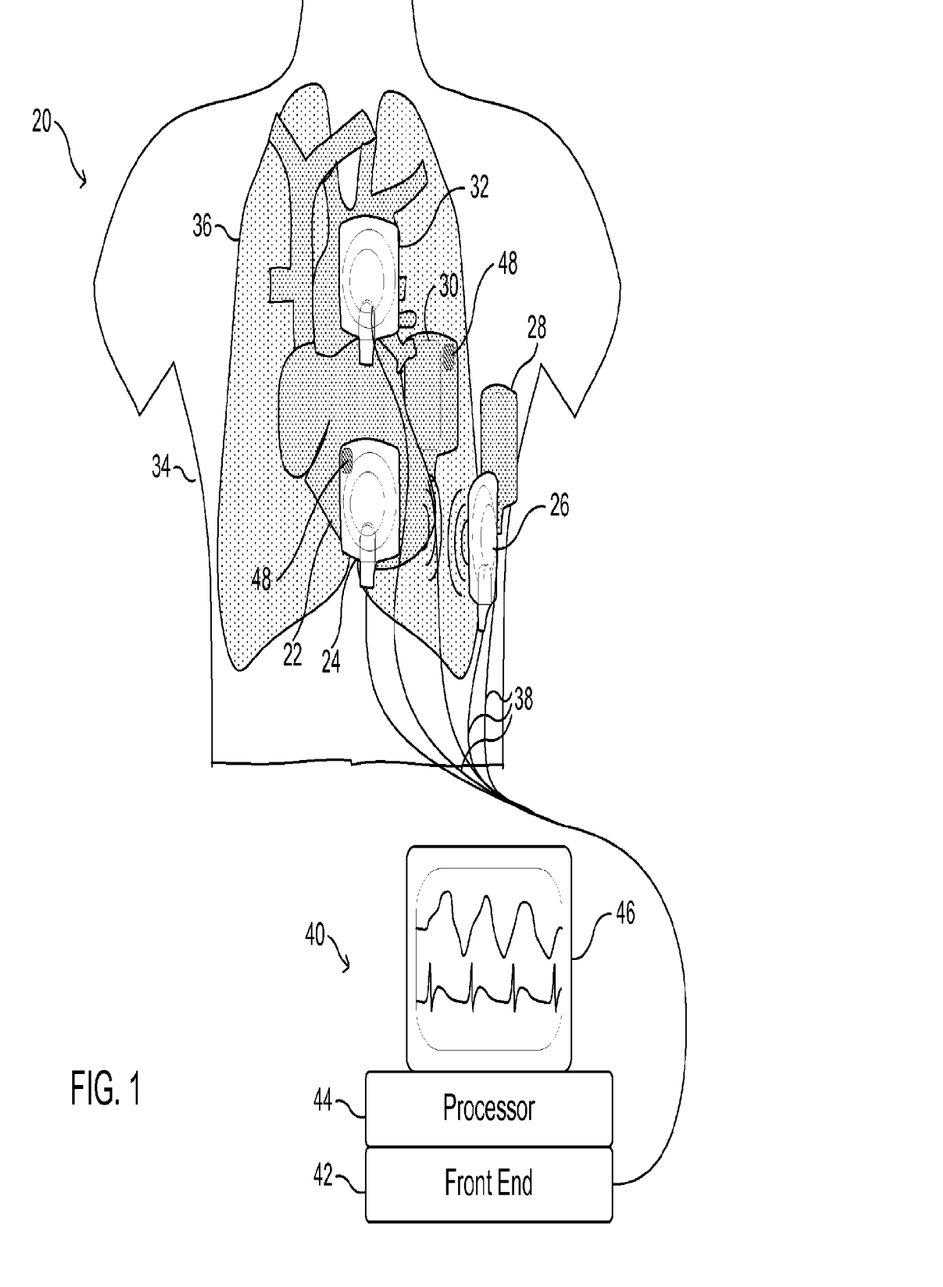
FIG. 1 is a schematic, pictorial illustration showing a system for monitoring of heart function, in accordance with an embodiment of the present invention.

FIG. 1 is a schematic, pictorial illustration of a system 20 for monitoring the function of a heart 22, in accordance with an embodiment of the present invention. Multiple antennas 24, 26, 28, 30, 32 are disposed at different, respective locations around a thorax 34 of the patient. (The thorax is transparent in the figure so as to make visible heart 22 and lungs 36, as well as antennas 28 and 30 on the patient's side and back.) The antennas in this embodiment partially surround the thorax. In alternative embodiments, a larger number of antennas may surround the thorax completely. In other embodiments, a smaller number of antennas, possibly only one or two antennas, may be used. The use of three or more antennas, however, is advantageous in providing multi-dimensional heart motion data, as explained further hereinbelow.

Typically, for good RF coupling, antennas 24, 26, 28, 30, 32 are fixed to the skin of the torso. For this purpose, the antennas may have the form of adhesive patches, as described in greater detail with reference to FIG. 4, for example. Additionally or alternatively, for improved coupling, a dielectric gel may be spread between the front surfaces of the antennas and the skin, as described, for example, in the above-mentioned PCT/IB2009/055438. This gel may have a high dielectric constant at microwave frequencies, to give good RF impedance matching, and high conductivity at low frequencies to enhance electrocardiogram signal acquisition. Further additionally or alternatively, the antennas may be attached to and held in place by a suitable garment, such as a vest (not shown), which the patient wears during the monitoring procedure. Typically, the procedure takes a short time, on the order of a few hours or less, although it is possible to monitor patients in this manner over the course of a day or even several days.

Antennas 24, 26, 28, 30, 32 are connected by cables to a control console 40. The console comprises a front end 42, which drives the antennas to direct RF electromagnetic waves from different, respective directions toward heart 22. In response to the waves that are scattered from the heart (and from other features in the body), the antennas output RF signals. Front end 42 receives these signals via cables 38, filters and digitizes the signals, and passes the resulting digital samples to processing circuitry 44. This processing circuitry processes the RF signals over time so as to provide a multi-dimensional measurement of movement of the heart, as shown and described below. Typically, processing circuitry 44 comprises a general-purpose computer processor, which is programmed in software to carry out the functions described herein. Additionally or alternatively, processing circuitry 44 may comprise dedicated or programmable hardware logic circuits.

In the pictured embodiment, processing circuitry 44 drives a display 46 to show a measurement of the movement of the heart, either graphically or numerically, or both. Additionally or alternatively, the processing circuitry may make other measurements based on the RF signals, such as measuring the amount of fluid accumulated in lungs 36, as described in greater detail hereinbelow. Further additionally or alternatively, front end 42 may receive ECG signals from the antennas on the body surface, and processor 44 may process and output ECG information in addition to measurement of heart motion. The combination of ECG and motion measurement in a single unit is efficient and useful in providing a complete picture of heart function, both electrical and mechanical.

In some embodiments, it is useful to know the precise locations, and possibly also the orientations, of the antennas. For this purpose, antennas 24 and 30 are shown in the figure as comprising position sensors 48. (The other antennas may also comprise position sensors, but these sensors are omitted from the figures for the sake of simplicity.) Various types of position sensors that are known in the art, such as magnetic, ultrasonic, optical or even mechanical position sensors, may be used for this purpose. PCT/IB2009/055438 includes further details of such position sensors and their integration in a radar-based measurement system.

Figure 2:
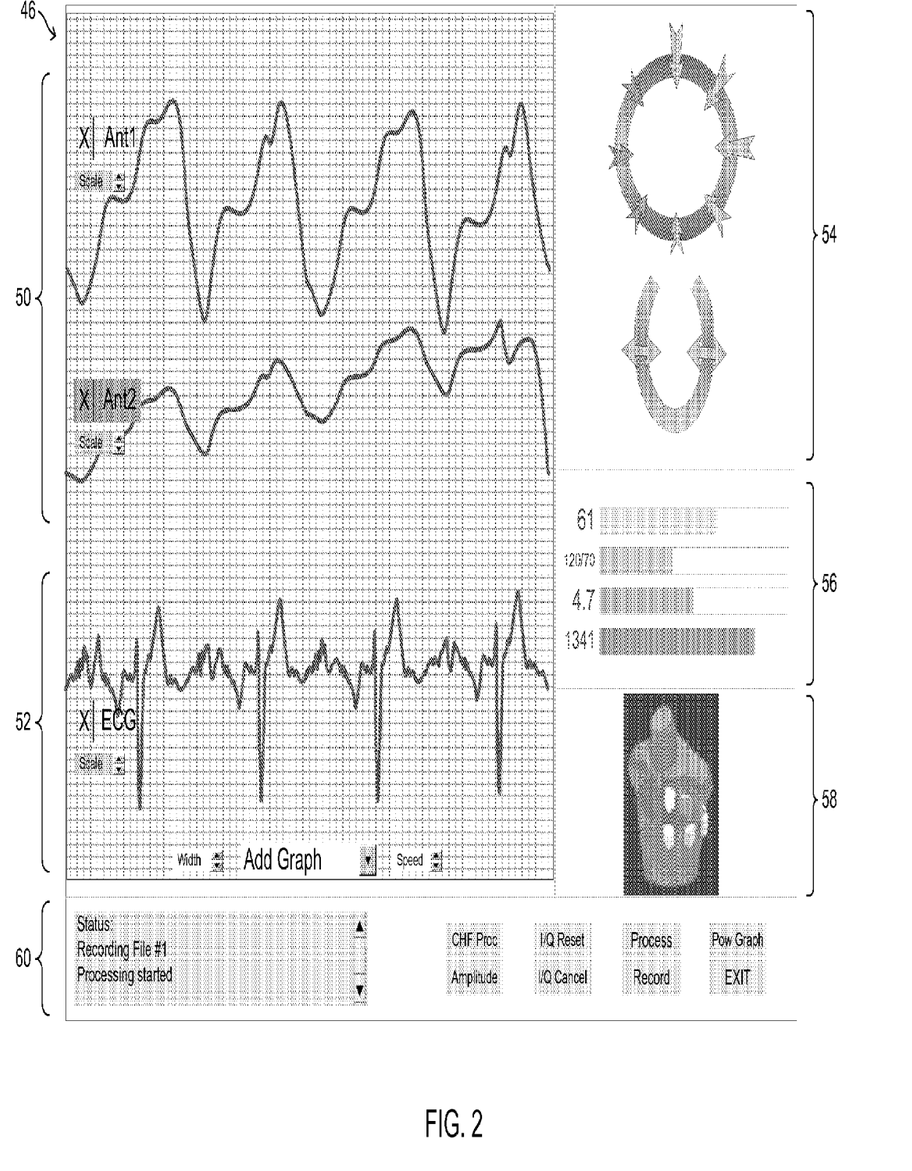
FIG. 2 is a schematic representation of a display screen in a system for monitoring of heart function, in accordance with an embodiment of the present invention.

FIG. 2 is a schematic representation of the screen of display 46 in system 20, in accordance with an embodiment of the present invention. Typically, the display is configurable by the user to show different measurements in various different formats. In the example shown in FIG. 2, display 46 shows traces 50 that are indicative of the motion of selected points on the heart wall over time, as measured by system 20. An ECG trace 52 is displayed alongside the wall motion traces for comparison. (Although only two motion traces and one ECG trace are shown in FIG. 2 for the sake of simplicity, a larger number of traces may alternatively be displayed.)

A graphical window 54 gives a two-dimensional (2D) view of the measured heart motion and also enables the user to choose the points whose motion is to be shown by traces 50. Alternatively, given a sufficient number of measurement points around the heart, window 54 may show a real-time three-dimensional (3D) representation of heart wall motion.

Display 46 may optionally include other information and user interface features. For example, a parameter window 56 may show parameters derived from the measurements made by system 20, such as cardiovascular and/or respiratory parameters, in either graphical or numerical form (or both). A status window 58 shows the current status of each of the antennas. This window may indicate, for example, an antenna that is not properly attached to the body (based on measurement of impedance between the antenna and the skin or on characteristics of the RF signals from the antenna), so that the operator can correct the situation. A control window 60 displays status messages and operational buttons to turn system functions on and off.

Figure 3:
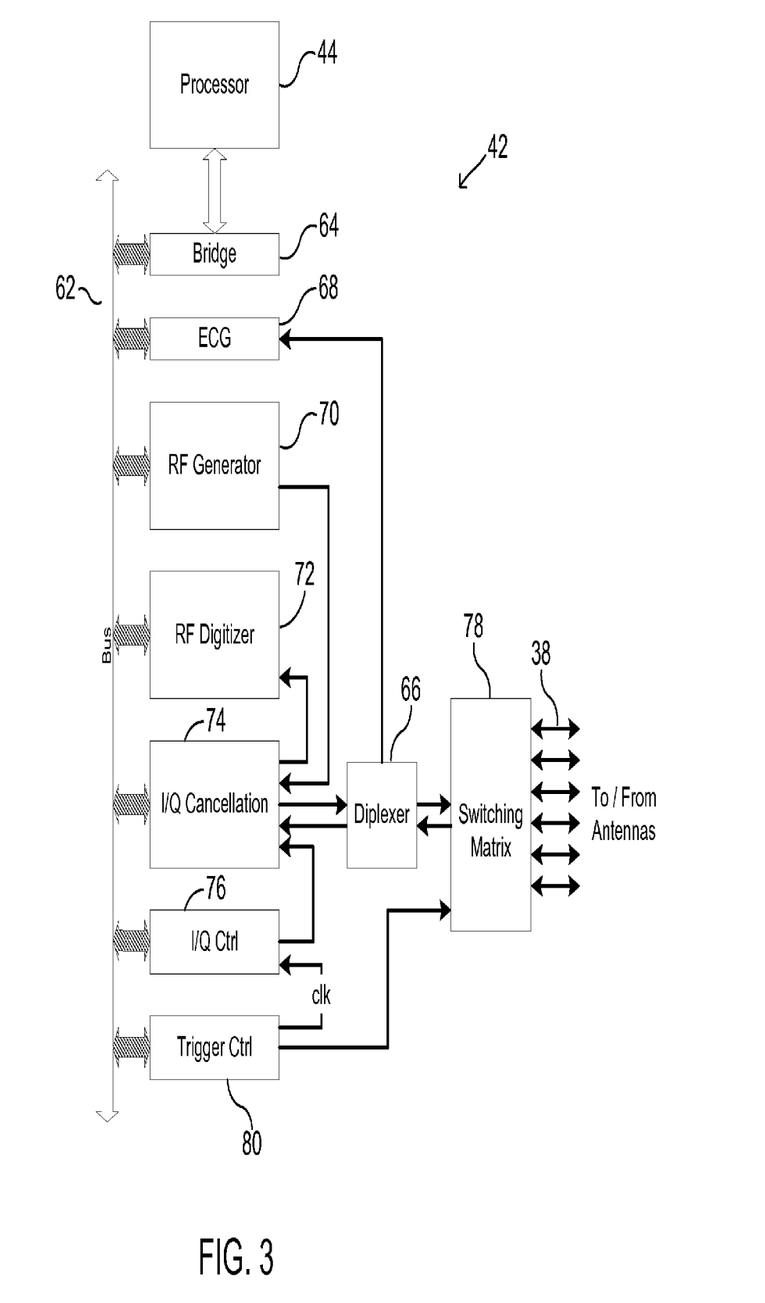
FIG. 3 is a block diagram that schematically shows functional elements of a system for monitoring of heart function, in accordance with an embodiment of the present invention.

FIG. 3 is a block diagram that schematically shows functional elements of system 20, and specifically of front end 42, in accordance with an embodiment of the present invention. The elements of the front end exchange data and control instructions via a high-speed bus 62, which is connected to processing circuitry 44 via a bridge 64. To enable ECG measurements, antennas 24, 26, 28, 30, 32 are connected via cables 38 and a switching matrix 78 to a diplexer 66 at the input to front end 42. The diplexer separates out the low-frequency ECG signals from the RF signals, passing the ECG signals to an ECG preprocessing circuit 68. This circuit filters and digitizes the ECG signals and passes the ECG data via bus 62 to processing circuitry 44.

Front end 42 comprises a RF generator 70, which serves as a driver circuit to generate signals at multiple different frequencies for exciting the transmitting antennas. A RF digitizer 72 demodulates and digitizes the signals received by the receiving antennas. Typically, the signals are in the range of about 400 MHz to about 4 GHz, although higher and lower frequencies outside this range may also be used. An I/Q cancellation unit 74 performs signal conditioning functions, including amplification of the outgoing and the incoming signals and cancellation of background components in the received signals. The background cancellation functions of unit are controlled by an I/Q controller 76, as is described in greater detail hereinbelow.

Switching matrix 78 selects different sets of the antennas to transmit and receive signals at different, respective times and frequencies, in a predetermined temporal pattern. Typically, the sets comprise pairs of antennas—one transmitting and one receiving. Alternatively, the switching matrix may select a set consisting of a single monostatic antenna, which both transmits and receives. Further alternatively, other antenna groupings may also be used. The structure and operation of a switching matrix of this sort are described in detail in PCT/IB2009/055438. Switching matrix 78 and RF generator 70 together serve as excitation circuitry and generate a temporal excitation pattern comprising a sequence of measurement frames, wherein each frame typically defines a sweep of the excitation signal both in frequency and over spatial channels (antennas or antenna pairs). The beginning of each frame is triggered by a trigger controller 80, which also provides a clock input to the other components of front end 42.

The sweep over multiple different frequencies creates, in effect, an ultra-wideband signal, which is equivalent, in the signal processing domain, to a very short radar pulse. The use of this sort of ultra-wideband signal enables system 20 to measure path length and heart wall range more accurately and robustly than can generally be achieved using narrow-band methods that are known in the art. Although system 20 is shown and described as comprising multiple antennas at different locations on the patient's thorax, the ultra-wideband approach described here may alternatively be used advantageously in measurements of heart wall movement using only a single antenna.

The functions of I/Q cancellation unit 74 are also described in detail in PCT/IB2009/055438. Briefly, unit modifies the phase and amplitude of the sampled signals from RF digitizer 72, under the control of I/Q controller 76, so as to generate an anti-phased signal matching a background component that is to be canceled. This background component may, for example, be a constant and/or slowly-varying part of the incoming signals, which is canceled in order to enhance the time-varying signal component that is due to heart motion. The I/Q cancellation unit generates a signal that is equal in amplitude to the background component but 180° out of phase and adds this anti-phased signal to the received signal from switching matrix 78 and digitizer 72. The I/Q cancellation unit thus cancels the background component without degrading the actual radar signal from the body.

Processing circuitry 44 collects samples of the received signals, following background cancellation, and processes the samples to identify and locate reflecting volumes within the thorax that correspond to points on the heart surface. One method that may be used for this purpose is the inverse spherical Radon transform. More specifically, PCT/IB2009/055438 describes a first-order approximation of the inverse spherical Radon transform, which can be applied efficiently and effectively to the sampled RF signals.

Alternatively, processing circuitry 44 may apply other transform techniques. For example, the processing circuitry may compute a frequency response vector for each pair of antennas, and may then apply a window function, such as a Kaiser window, to each vector and transform the windowed frequency data to the time domain using an inverse Fast Fourier Transform (FFT). A time-domain filter, such as a Kalman filter, may be applied to the transformed data in order to model the location and motion of the heart wall. The processing circuitry may correlate location and motion data between different antenna pairs, as well as correlating the motion with ECG measurements. Additionally or alternatively, circuitry may perform ECG-gated or ECG-phased background subtraction, wherein the subtracted background signal is computed as a combination of the different phases in the heartbeat.

In estimating the heart wall location, circuitry 44 may treat the returned signal as a superposition of a number of point reflectors, each moving and scintillating at a predefined rate and in a predefined manner. The locations of the point reflectors are estimated using optimization techniques, such as a modified simplex technique. The estimated locations are then used to calculate path length and amplitude and thereby to calculate heart wall movement and/or liquid content of the lungs.

Further additionally or alternatively, processing circuitry 44 may receive and process other physiological parameters in conjunction with the RF signals. For example, the processing circuitry may receive breathing information, as well as data concerning patient posture, patient weight, and blood pressure.

Antenna Design

Figure 4:
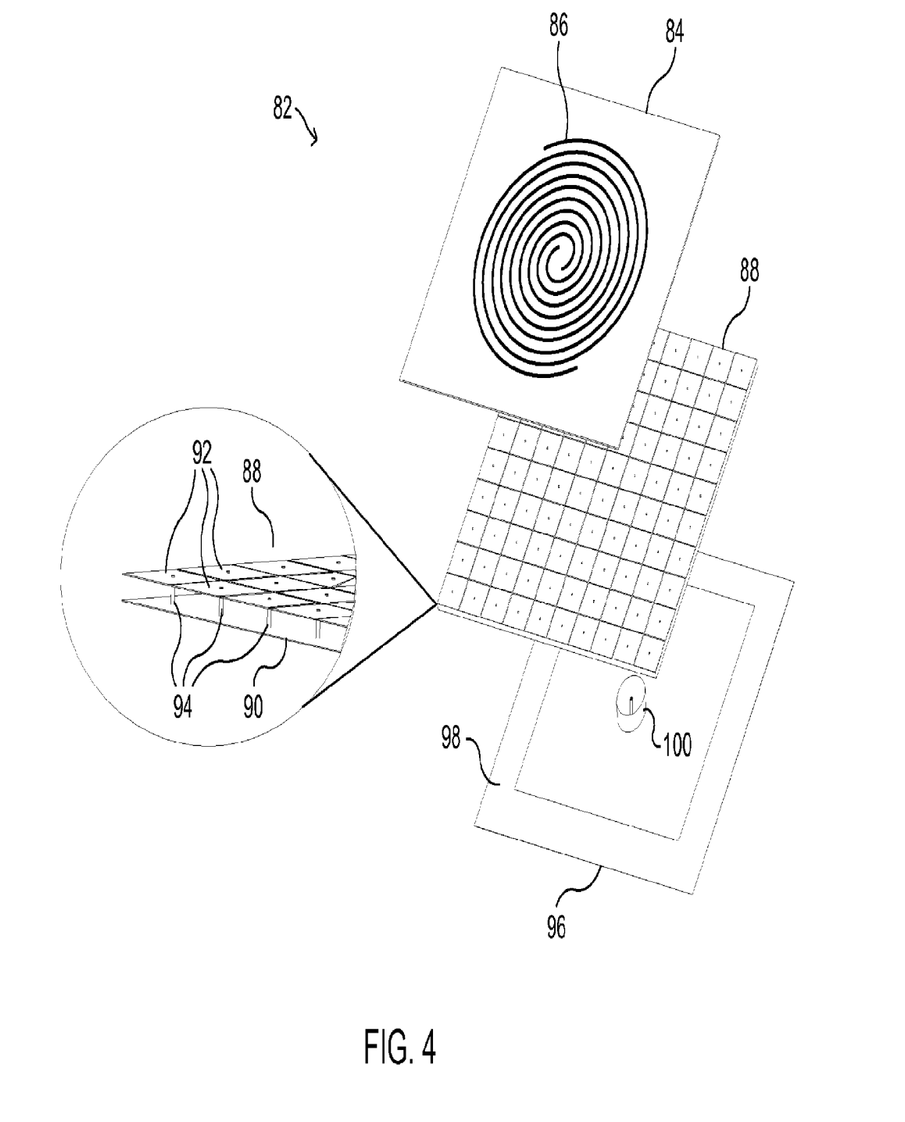
FIG. 4 is a schematic exploded view of a patch antenna, in accordance with an embodiment of the present invention.

FIG. 4 is a schematic exploded view of a patch antenna unit 82, in accordance with an embodiment of the present invention. The pictured antenna design may be used, for example, for any or all of the antennas shown in FIG. 1, as well as the antennas in the figures that follow. This design is suitable for production as a flexible patch, similar to a large ECG electrode, which can be glued onto the body surface with a suitable adhesive. Antenna unit 82 is shown solely by way of example, however, and other types of antennas may similarly be used in system 20, as well as in the embodiments that are described below.

Antenna unit 82 comprises a front surface 84 in the form of a planar printed circuit board (PCB), on which a conductive spiral 86 is printed to serve as the radiating element of the antenna, using methods of printed circuit fabrication that are known in the art. The front surface is made of suitable biocompatible materials in order to be brought into contact with the body surface. (A layer of gel may be applied between front surface 84 and the body surface, as explained above.) A rear element 88 of the antenna, behind the front surface, serves as a reflective structure. Element 88 comprises a ground plane and a periodic structure that create an electromagnetic band gap (EBG) between the ground plane and the front surface. Details of the theory and design of this sort of antenna are provided by Bell et al., in "A Low-Profile Archimedean Spiral Antenna Using an EBG Ground Plane," *IEEE Antennas and Wireless Propagation Letters* 3, pages 223-226 (2004), which is incorporated herein by reference.

The EBG structure in antenna unit 82 is made up of a periodic mesh of conductive patches 92, which are connected to ground plane 90 by vias 94 through a thin dielectric layer (omitted from the figure for visual clarity). The periodic mesh of rear element 88 can have Cartesian or cylindrical symmetry. Since different frequencies exhibit different power densities at different locations on the rear element surface, the components of the EBG structure can have variable dimension to reflect the different frequencies accordingly. For the frequency range mentioned above (400 MHz to 4 GHz), the PCB making up front surface 84 may be 1.6 mm thick, for example, while patches 92 are spaced 1.6 mm from ground plane 90 and contact the rear side of the front surface PCB when assembled. The thickness of front surface 84 and the height of the EBG (as defined by vias 94) can be optimized for the target VSWR performance, front lobe pattern and gain. Under these conditions, the mesh of patches 92 creates an array of cavities having a parallel resonant response that mimics a perfect magnetic conductor in the specified frequency range. The EBG structure thus reflects the backward wave from spiral 86 in phase with the forward beam, thereby constructively adding to the main forward beam from the antenna.

A flexible backing 96 covers the rear side of rear element 88. Backing 96 extends over the edges of the front surface and rear element in order to facilitate secure attachment of antenna unit 82 to the body surface. For this purpose, backing 96 may comprise an adhesive margin 98. Backing 96 may comprise a conductive element for receiving ECG signals from the body surface. Alternatively, front surface 84 may contain such a conductive element (not shown) alongside spiral 86, or the conductive spiral itself may serve to pick up the ECG signals. Additionally or alternatively, the antenna can be coated with metal and electrolytes to enable ECG measurement without affecting RF performance. A RF connector 100 connects antenna unit 82 to cable 38. This connector conveys the RF excitation signal to spiral 86 and returns both RF and ECG signals from the antenna unit to the cable.

Assessment of Pulmonary Edema

Referring back to FIG. 1, some of antennas 24, 26, 28, 30 and 32 are positioned in such a way that the RF waves they emit and/or receive pass through one of lungs 36. For example, when antenna 26 operates in monostatic mode, it directs RF waves through the left lung toward heart 24 and then receives reflected waves from the heart back through the left lung. As another example, in bistatic mode, antenna 30 receives RF waves emitted by antenna 24 after transmission through the lung. The RF path length in either case will vary over the respiration cycle, as the lung fills with air and then empties, and it will vary depending on the amount of fluid accumulated in the lung. Processing circuitry 44 may analyze these path length variations in order to assess the amount of fluid accumulation in the lung.

Figure 5A:
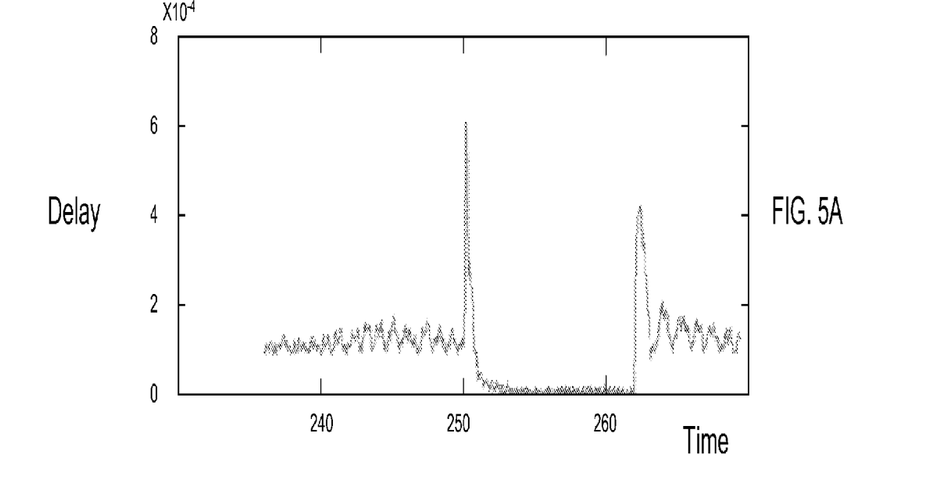
FIGS. 5A and 5B are schematic plots of propagation delay and amplitude, respectively, of RF waves reflected from the heart, in accordance with an embodiment of the present invention.
Figure 5B:
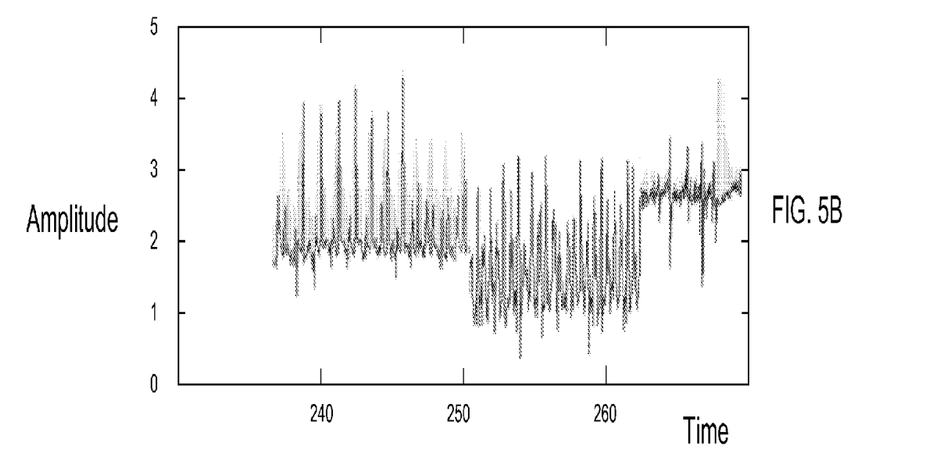

FIGS. 5A and 5B are schematic plots of propagation delay and amplitude, respectively, of RF waves reflected from the heart, in accordance with an embodiment of the present invention. These plots represent measurements made on a healthy subject using an antenna configured and positioned similarly to antenna 26. The scales are arbitrary. The delay and, to a lesser extent, the amplitude vary periodically with the heart cycle, as shown particularly by the sharp peaks in FIG. 5A.

The depressed portions of both plots between marks 260 and 290 on the horizontal scale correspond to a period of inhalation during the respiratory cycle. This depression in FIG. 5A shows that when the lungs are full of air, the effective RF path length through the lung decreases, since the physical distance between antenna 24 and heart 22 remains about the same, while the average dielectric constant along the path decreases. Exhalation empties the lungs of air and thus increases the effective RF path length. The amplitude of the reflected wave in FIG. 5B also drops during inhalation, presumably because of increased variations of the dielectric constant, and hence more reflections, along the RF path through the lung when the lung is filled with air.

For a lung with a high fluid content, the average dielectric constant will typically be higher than a healthy lung, and the path delay of RF waves traversing the lung will therefore be greater. The overall amplitude may also be greater due to reduced reflections as the waves traverse the lungs. On the other hand, the difference between air-filled and empty lungs over the respiratory cycle is expected to be smaller in both delay and amplitude than the differences shown in FIGS. 5A and 5B. Thus, to diagnose and monitor pulmonary edema, processing circuitry 44 may, for example, compare the delay and possibly the amplitude of the reflected waves to benchmarks provided by healthy and edematous lungs, or to previous measurements made on the same patient. Additionally or alternatively, the processing circuitry may assess the amount of fluid in the lungs by analyzing the changes in delay and/or amplitude of the reflected waves over the course of one or more respiratory cycles.

In order to quantify the assessment of fluid accumulation, the actual physical distance traversed by the RF waves passing through the lung may be measured, and a relation (such as a ratio) may be computed between the effective RF path length and the physical distance. For example, referring back to FIG. 1, if antennas 24 and 30 on opposite sides of the thorax are used to make a transmission-based measurement of the RF path length through lung 36, the physical distance between these antennas may also be measured. One way to measure the physical distance is by mechanical measurement, using a large caliper, for example. Alternatively or additionally, position sensors 48 attached to the antennas may be used to compute the spatial coordinates of each antenna, and the physical distance may then be computed simply as the Cartesian distance between the coordinate points.

Figure 6:
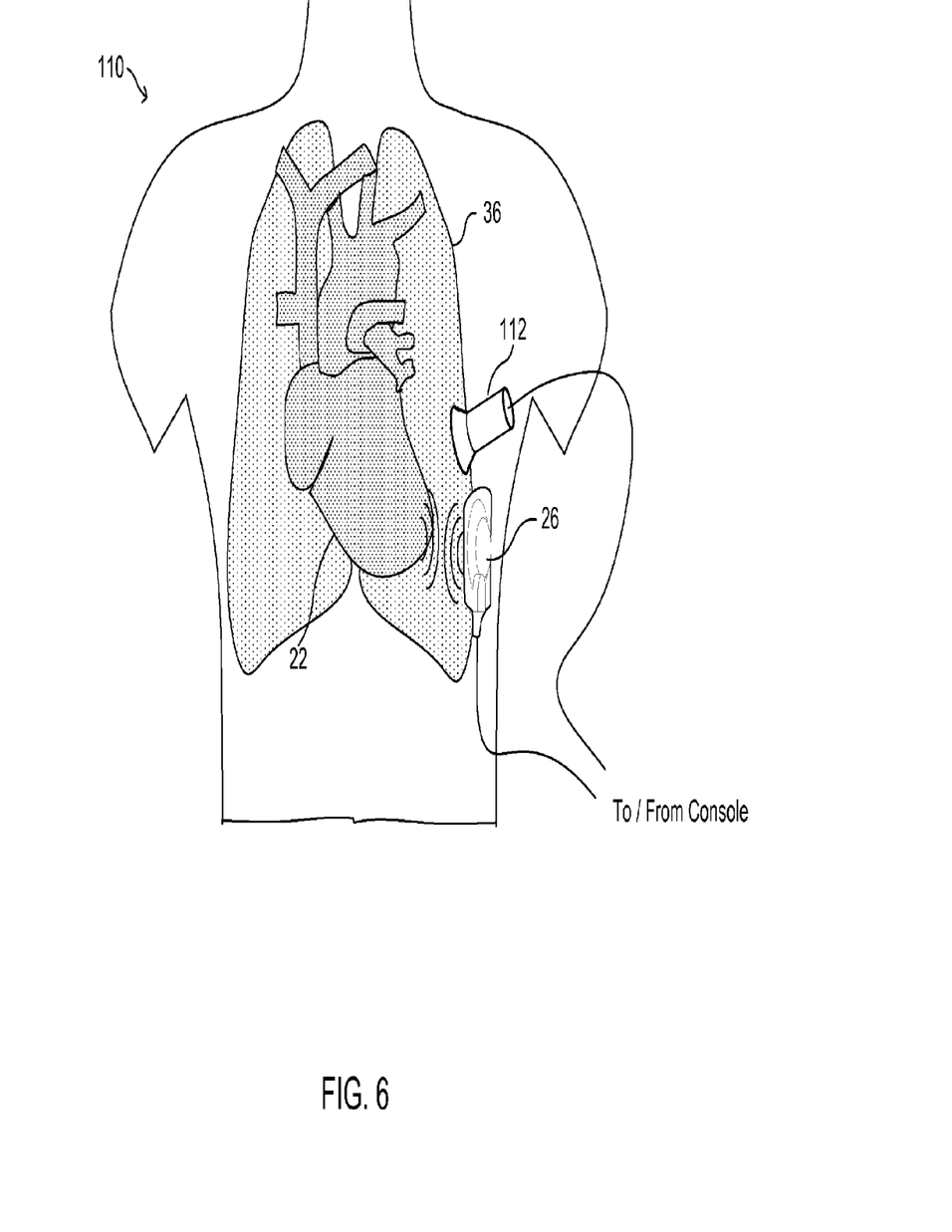
FIG. 6 is a schematic, pictorial illustration showing elements of a system for diagnosis of pulmonary edema, in accordance with an embodiment of the present invention.

FIG. 6 is a schematic, pictorial illustration showing elements of a system 110 for diagnosis of pulmonary edema, in accordance with an embodiment of the present invention. In this embodiment, antenna 26 is operated monostatically to measure the effective path length of RF waves that are reflected from heart 22 via lung 36. An ultrasound transducer 112 alongside antenna 26 is used to measure the physical distance to the heart and back. (Although antenna 26 and transducer 112 are shown, for the sake of clarity, as separate units, they may alternatively be integrated in a single package.) The heart wall is identified in both the RF and ultrasound data as the nearest significantly moving reflective surface.

Processing circuitry 44 computes the relation between the physical distance traversed by the ultrasonic waves and the effective path length traversed by the RF waves. Variations in this relation among different patients and among measurements at different points in time for a given patient are indicative of the amount of fluid in the lung.

Therapeutic Applications

Mechanical sensing of cardiac activity has been proposed for use in cardiac stimulation therapy, such as optimizing timing intervals during cardiac pacing. Detection of peak endocardial wall motion in the apex of the right ventricle for optimizing AV intervals has been validated clinically. Systems and methods for using cardiac wall motion sensor signals to provide hemodynamically-optimal values for heart rate and AV interval have been described, for example, in U.S. Pat. No. 5,549,650, whose disclosure is incorporated herein by reference. A cardiac stimulating system designed to automatically optimize both the pacing mode and one or more pacing cycle parameters in a way that results in optimization of a cardiac performance parameter, such as heart accelerations, is generally described in U.S. Pat. No. 5,540,727, whose disclosure is also incorporated herein by reference.

Figure 7:
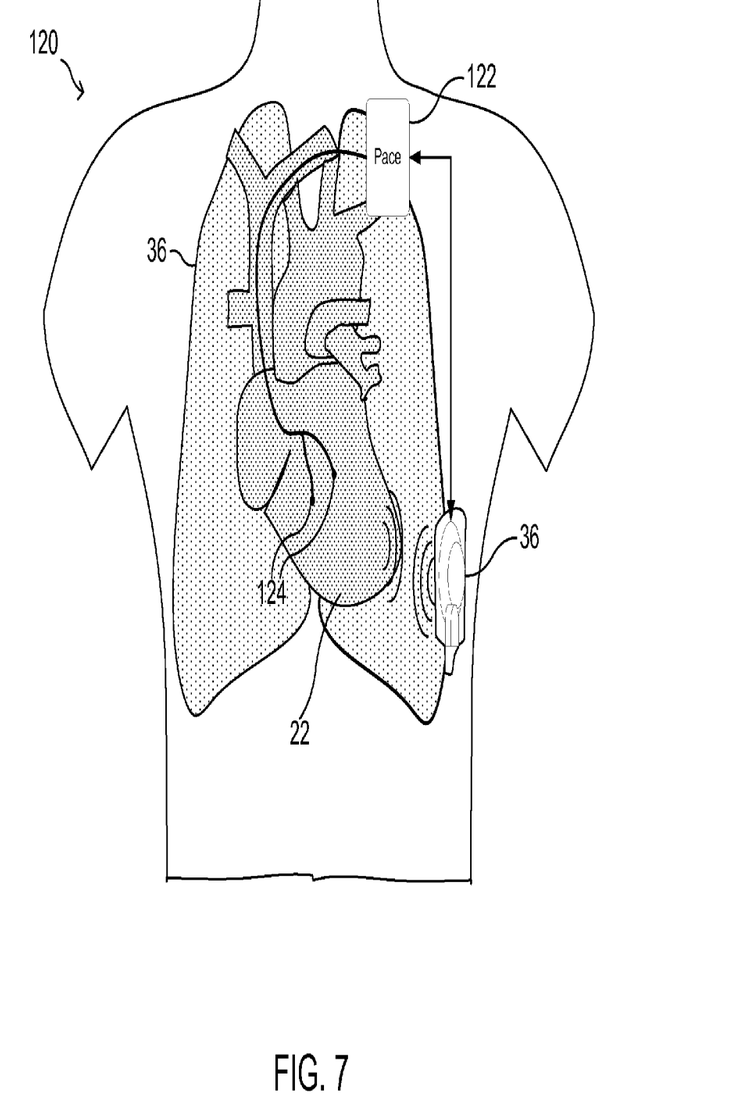
FIG. 7 is a schematic, pictorial illustration showing elements of a system for pacing the heart, in accordance with an embodiment of the present invention.

FIG. 7 is a schematic, pictorial illustration showing elements of a system 120 for pacing heart 22 based on measurements of heart wall motion, in accordance with an embodiment of the present invention. For the sake of simplicity, this figure shows a single antenna 26 used to measure motion of heart 22, but alternatively, multiple antennas may be used (as shown in FIG. 1, for example) to provide multi-dimensional wall motion data. A pacing circuit 122 receives and processes the RF signals from the antennas in order to measure the heart wall movement. Based on this measurement, the pacing circuit generates pacing signals to drive pacing electrodes 124 in the heart. The pacing circuit may adjust the timing and/or amplitude of the pacing signals adaptively, while measuring the wall movement, in order to reach an optimal therapeutic result.

As noted above, antenna 26 may also be used in assessing the fluid content of the lungs. The level of fluid content may then be used in adjusting the pacing regime of electrodes 124, as described, for example, in U.S. Pat. No. 7,191,000, whose disclosure is incorporated herein by reference.

Self-Contained Antenna Patch Unit

Figure 8:
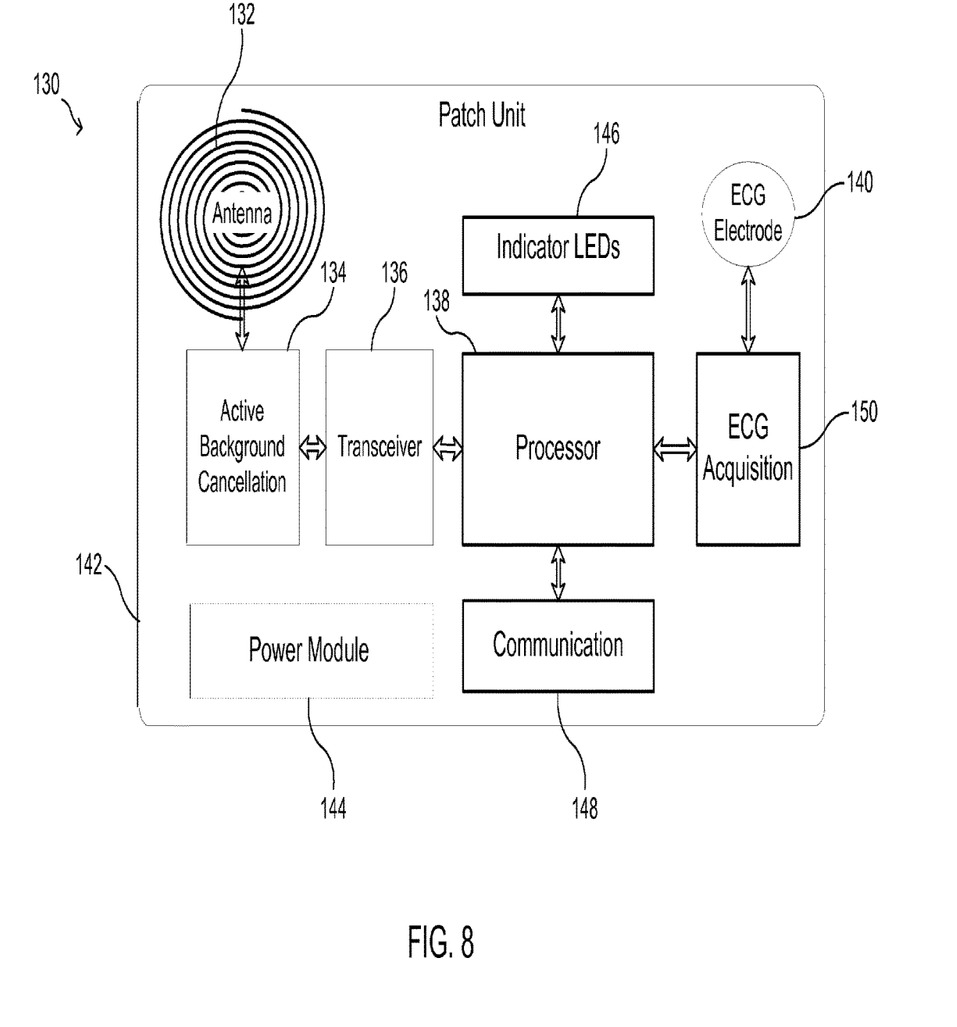
FIG. 8 is a block diagram that schematically illustrates a patch antenna unit, in accordance with another embodiment of the present invention.

FIG. 8 is a block diagram that schematically illustrates a patch antenna unit 130, in accordance with another embodiment of the present invention. Patch 130, in effect, performs most of the functions of system 20, using components that are contained inside an integrated package 142 having the form of a patch, which is typically no more than 20×50 mm across (and may be smaller). As in the preceding embodiments, package 142 may include an adhesive layer (as shown in FIG. 4, for example), by means of which unit 130 can be affixed to the patient's skin.

Patch unit 130 comprises a flat antenna 132, which may be of one of the types described above. A transceiver 136 generates driving signals for transmission by antenna 132 and filters and digitizes the reflected signals that the antenna receives from the patient's body. An active background cancellation circuit 134 cancels background components from the reflected signals, in a manner similar to that of I/Q cancellation unit 74, shown in FIG. 3. A processor 138 controls the operation of the other components of patch 130 and processes the digitized signals output by transceiver 136 in order to extract heart wall motion data, in a similar manner to processing circuitry 44. A power module 144, such as a low-profile battery, provides power to the components of the patch unit.

Patch unit 130 also comprises an ECG electrode 140, in electrical contact with the patient's skin, and an ECG acquisition circuit 150, which filters and digitizes the ECG signals for input to processor 138.

Patch unit 130 may comprise a user interface, such as one or more indicator LEDs 146, which signal the operational state of the patch (on/off, and possibly parameters such as battery level, quality of skin contact or signal strength). Alternatively or additionally, the user interface may comprise a more informative display, such as a LCD, as well as user controls, such as on/off and adjustment buttons.

A communication interface 148 communicates with a remote console (not shown), in order to transmit radar and ECG measurement data and possibly to receive operational commands. The communication interface typically comprises a wireless link, such as a Bluetooth™ or WiFi link. The console may be located in proximity to the patient's location and may thus receive data from interface 148 directly. Alternatively, interface 148 may communicate with a local gateway, such as a personal computer or smart phone, which communicates with the console over a network, such as the Internet or a telephone network. In this sort of embodiment, for example, the console may comprise a server, which stores the data for subsequent viewing and analysis by a physician or other expert. This sort of system configuration is particularly useful for extended ambulatory monitoring.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A diagnostic apparatus, comprising:
   one or more antennas configured to be disposed on a thorax of a body of a patient so as to direct radio frequency (RF) electromagnetic waves through a lung in the body and to output signals responsively to the RF electromagnetic waves that have passed through the lung; and
   processing circuitry configured to:
      process the signals to determine a path characteristic of the RF electromagnetic waves,
      compare the path characteristic to one or more benchmark path characteristic values corresponding to identified levels of fluid content of lungs, and
      determine fluid content of the lung based on the comparison.

2. The apparatus of claim 1, wherein the processing circuitry is further configured to measure a change in the path characteristic over one or more respiratory cycles of the lung, and to determine the fluid content responsively to the change.

3. The apparatus of claim 1, wherein the path characteristic comprises an effective RF path length of the RF electromagnetic waves through the body.

4. The apparatus of claim 1, wherein the benchmark path characteristic values comprise a physical distance traversed by the RF electromagnetic waves through the thorax of the body.

5. The apparatus of claim 4, wherein the one or more antennas comprise:
   a transmitting antenna at a first location on a first side of the thorax, which transmits the RF electromagnetic waves through the lung, and
   a receiving antenna, which receives the waves that have passed through the lung at a second location on a second side of the thorax, opposite the first side, and
   wherein the physical distance is measured between the first and second locations.

6. The apparatus of claim 4, wherein the one or more antennas comprise at least one antenna that is configured to direct the RF electromagnetic waves through the lung toward a heart in the body, and to output the RF signals responsively to the RF electromagnetic waves reflected from the heart.

7. The apparatus of claim 6, further comprising an ultrasonic transducer, which is adjacent to the at least one antenna and is configured to direct ultrasonic waves toward the heart and receive the ultrasonic waves reflected from the heart so as to provide a measure of the physical distance.

8. The apparatus of claim 1, wherein the path characteristic comprises an amplitude of the RF electromagnetic waves.

9. The apparatus of claim 1, wherein the path characteristic comprises a phase of the RF electromagnetic waves.

10. An apparatus for at least one of monitoring fluid level and diagnosis of a condition associated with fluid level, in tissue of a body, the apparatus comprising:
   one or more antennas configured for positioning on the body of a patient so as to direct radio frequency (RF) electromagnetic waves through a first tissue of the body and to output signals responsively to the RF electromagnetic waves that have passed through the first tissue; and
   processing circuitry configured to:
      process the signals at a plurality of different points over a period of time to determine a path characteristic of the RF electromagnetic waves relative to the first tissue at the different points, and
      determine a change in fluid content of the first tissue over the period of time based on a comparison of the determined path characteristics at the different points.

11. The apparatus of claim 10, wherein the path characteristic comprises an amplitude and/or a phase of the RF electromagnetic waves.

* * * * *